US006051387A

United States Patent [19]
Handley et al.

[11] Patent Number: 6,051,387
[45] Date of Patent: *Apr. 18, 2000

[54] METHODS OF DETERMINING THE PRESENCE OF A NEOPLASM WITH CLNH5- AND CLNH11-SPECIFIC ANTIBODIES

[75] Inventors: Harold H. Handley, Charlottesville, Va.; Mark C. Glassy, San Diego, Calif.; Hideaki Hagiwara, Osaka; Yoshihide Hagiwara, Uka, both of Japan

[73] Assignee: The Regents of the University of California, Oakland, Calif.

[*] Notice: This patent is subject to a terminal disclaimer.

[21] Appl. No.: 08/480,014

[22] Filed: Jun. 7, 1995

Related U.S. Application Data

[62] Continuation of application No. 08/443,810, May 18, 1995, which is a continuation of application No. 08/163,377, Dec. 7, 1993, abandoned, which is a division of application No. 07/113,212, Oct. 23, 1987, Pat. No. 5,286,647, which is a continuation-in-part of application No. 06/573,974, filed as application No. PCT/US83/00781, May 20, 1983, abandoned, and a continuation-in-part of application No. 06/465,081, Feb. 9, 1983, Pat. No. 4,618,577.

[30] Foreign Application Priority Data

May 21, 1982 [JP] Japan ...................................... 57-84843

[51] Int. Cl.[7] .................................................... G01N 33/53
[52] U.S. Cl. ........................... 435/7.23; 435/7.1; 435/7.2; 435/7.21
[58] Field of Search ............................... 424/130.1, 1.11, 424/1.49, 138.1, 141.1, 142.1, 155.1, 174.1; 530/387.1, 387.3, 388.15, 388.8; 435/70.21, 170.6, 240.67, 7.1, 7.2, 7.21, 7.23

[56] References Cited

U.S. PATENT DOCUMENTS

| | | |
|---|---|---|
| 3,654,090 | 4/1972 | Schuurs . |
| 3,927,193 | 12/1975 | Hansen et al. . |
| 4,172,124 | 10/1979 | Koprowski et al. . |
| 4,331,647 | 5/1982 | Goldenberg . |
| 4,348,376 | 9/1982 | Goldenberg . |
| 4,350,626 | 9/1982 | Masuho et al. . |
| 4,359,457 | 11/1982 | Neville, Jr. et al. . |
| 4,361,544 | 11/1982 | Goldenberg . |
| 4,434,230 | 2/1984 | Ritts, Jr. . |
| 4,443,427 | 4/1984 | Reinherz et al. . |
| 4,444,887 | 4/1984 | Hoffman . |
| 4,451,570 | 5/1984 | Royston et al. . |
| 4,454,106 | 6/1984 | Gansow et al. . |
| 4,464,465 | 8/1984 | Lostrom . |
| 4,618,577 | 10/1986 | Handley et al. . |
| 4,618,585 | 10/1986 | Chan . |
| 4,693,966 | 9/1987 | Houghton et al. . |
| 4,761,377 | 8/1988 | Glassy . |
| 5,286,647 | 2/1994 | Handley . |
| 5,589,573 | 12/1996 | Hagirawa et al. . |

FOREIGN PATENT DOCUMENTS

| | | |
|---|---|---|
| 0 044 722 | 1/1982 | European Pat. Off. . |
| 0 44 722 | 1/1982 | European Pat. Off. . |
| 62-409 | 10/1982 | European Pat. Off. . |
| 2 086 937 | 11/1981 | United Kingdom . |
| 2 113 715 | 1/1982 | United Kingdom . |
| 82/ 01461 | 5/1982 | WIPO . |
| 83/ 00503 | 2/1983 | WIPO . |
| 83/ 04313 | 12/1983 | WIPO . |

OTHER PUBLICATIONS

Hagirawa et al. Mol. Biol. Med. 1: 245–252, (1983).

Aotsuka et al. Mem. Fac. Sci. Kyoto Univ. 12: 1–10, (1987).

AtCC Cell Lines and Hybridomas, Eigth Edition, 1994 Ed Hay et al. Rockville MD 1994 pp. 206–207.

James et al. J. Immunol. Methods 100: 5–40 (1987).

Glassy et al. Fed. Proc. 40: 996 (1981) abstract #4340.

Pickering et al. J. Immonol. 129: 406–412 (1982).

Paul @ Fundalmental Immunology, Review Press 1993 p 242 only.

Brown, J., et al., "Use of Monoclonnal Antibodies for Quantitative Analysis of Antigens in Normal and Neoplastic Tissues", (1981) *Clin. Chem.* 27(9):1592–1596.

Cote, R., et al., "Generation of Human Monoclonal Antibodies Reactive With Cellular Antigens", (Apr., 1983) *Proc. Natl. Acad. Sci.* 80:2026–2030.

Gilliland, D.G., et al., "Antibody–Directed Cytotoxic Agents: Use of Monoclonal Antibody to Direct the Action of Toxin A Chains to Colorectal Carcinoma Cells", (Aug. 1980) *Proc. Natl. Acad. Sci.* 77(8):4539–4543.

Glassy, M., et al., "A Human Monoclonal Antibody Reactive Against a Human Tumor–Associated Antigen" (Abstract), (Mar. 1, 1982) *Federation Proceedings*, 41(3):1657.

Glassy, M., et al., "An Enzyme Immonofiltration Assay Usefull for Detecting Human Monoclonal Antibody" (1983) *Journal of Immunological Methods*, 58:119–126.

Glassy, M., et al., "UC 729–6, A Human Lymphoblastoid B–Cell Line Useful for Generaing Antibody–Secreting Human–Human Hybridomas" (Oct. 1983) *Proc. Natl. Acad. Sci.*, 80(20):6327–6331.

Handley, H., et al., "The Production of Human Monoclonal Antibodies to Human Tumor Associated Antigens", (Abstract) (Dec. 1982) *15th International Leucocyte Conference, Asilomar, Immunobiol*, 163:287.

Irie, R., et al., "Human Antibody to OFA–I, a Tumor Antigen, Produced In Vitro by Epstein–Barr Viris–Transformed Human B–Lymphoid Cell Lines" (Sep. 1982) *Proc. Natl. Acad. Sci.*, 79:5666–5670.

(List continued on next page.)

*Primary Examiner*—Christina Y. Chan
*Assistant Examiner*—Phillip Gambel
*Attorney, Agent, or Firm*—Majestic, Parsons, Siebert & Hsue P.C.

[57] ABSTRACT

CLNH5 and CLNH11-specific hybridomas, human monoclonal antibodies and their uses are provided. The antibodies distinguish a human neoplastic cell from a normal cell of the same tissue type. The monoclonal antibodies find use in therapy and diagnosis, both in vitro and in vivo.

6 Claims, No Drawings

OTHER PUBLICATIONS

Irie. R., et al., "In Vitro Production of Human Antibody to a Tumor–Associated Foetal Antigen" (1981) Br. J. Cancer, 44:262–266.

Kohler–Milstein, "Continuous Cultures of Fused Cells Secreting Antibody of Predefined Specificity", (Aug. 7, 1975) Nature, 256:495–497.

Raso, V., et al., "Monoclonal Antibody–Ricin A Chain Conjugate Selectively Cytotoxic for Cells Bearing the Common Acute Lymphoblastic Leukemia Antigen" (Feb. 1982) Cancer Research, 42:457–464.

Schlom, J., et al., "Generation of Human Monoclonal Antibodies Reactive With Human Mammary Carcinoma Cells", (Nov. 1980) Proc. Natl. Acad. Sci., 77(11):6841–6845.

Schlom, J., et al., "Generation and Characterization of Murine and Human Monoclonal Antibodies Reactive with Human Mammmary Tumor Cells", (1982) Hybridomas in Cancer Diagnosis and Treatment, :213–214, Mar. 11, 1994.

Schwaber, J., Cohen, E., "Human X Mouse Somatic Cell Hybrid Clone Secreting Immunoglobulins of Both Parental Types" (Aug. 17, 1973) Nature, 244:444–447.

Teramoto Y.A., et al., "The Immunohistochemical Reactivity of a Human Monoclonal Antibody with Tissue Sections of Human Mammary Tumors", (Jul. 15, 1982) Cancer, 50:241–249.

Wunderlich, D., et al., "The Use of Lymphocytes From Auxillary Lymph Nodes of Mastectomy Patients to Generate Human Monoclonal Antibodies", (1981) Eur. J. Cancer Clin. Oncol., 17(7):719–730.

Olsson, L. and Kaplan, H.S., "Human–human hybridomas producing monoclonal antibodies of predefined antigenic specificity", (1980) Proc. Natl. Acad. Sci. USA 77(9):5429–5431.

METHODS OF DETERMINING THE PRESENCE OF A NEOPLASM WITH CLNH5- AND CLNH11-SPECIFIC ANTIBODIES

CROSS REFERENCE TO RELATED APPLICATION

This application is a continuation of U.S. application Ser. No. 08/443,810, filed May 18, 1995, which is a continuation of U.S. application Ser. No. 08/163,377, filed Dec. 7, 1993, now abandoned which is a divisional of U.S. application Ser. No. 07/113,212, filed Oct. 23, 1987, now U.S. Pat. No. 5,286,647, which is a continuation-in-part of 06/573,974, filed Feb. 21, 1984, now abandoned, which is a U.S. National Phase of PCT/US83/00781, which claims priority to Japanese Application No. JP84843-3 and is a continuation-in-part of U.S. application Ser. No. 06/465,081, filed Feb. 9, 1983, which issued as U.S. Pat. No. 4,618,577.

BACKGROUND OF THE INVENTION

1. Field of the Invention

The mammalian immune system has a matchless ability to produce molecules with specificity and avidity for a particular spatial and polar structure, as may be found with sequences of amino acids and sugars. For a long period of time, one was dependent upon producing antibodies employing the immune system in vivo. The resulting polycolonal antibodies demonstrated high specificity for a specific antigen, but could not discriminate between various sites on the antigen and, furthermore, were a mixture of antibodies of varying specificity and avidity. Thus, one observed the averaging over the entire composition and not the properties of a specific antibody.

With the seminal discovery by Milstein and Kohler, one can now produce homogeneous compositions of antibodies by fusing a B-lymphocyte with a myeloma cell to produce a cell referred to as a hybridoma. For the most part, the use of this technology has been limited to mouse cells, where stable myeloma lines have served as fusion partners to provide stable hybridomas which can be produced with high efficiency and are capable of being maintained as productive entities over long periods of time. Higher organisms, particularly humans, have proven to be much more intractable in developing fusion partners and hybridomas. However, in 1980, the first human fusion partner was reported by Drs. Olsson and Kaplan and since that time, an additional few human fusion partners have been reported. Nevertheless, the preparation of hybridomas by human-human crosses has remained difficult due to problems of efficiency in fusion, culturing the cells, and maintaining their productive capabilities. However, because of the many advantages of having human hybridomas which produce antibodies allogenic to a human host, particularly for in vivo applications, human hybridomas remain of great interest. In other instances, even with the difficulties encountered with human-human crosses, the human hybridoma may be preferable to a heterogenic cross, where the resulting hybridoma may lose the genetic information for the monoclonal antibodies (MoAbs) after a number of passages.

One of the areas of interest for the use of monoclonal antibodies is in diagnosing and treating cancer. Monoclonal antibodies for these purposes desirably are specific for a particular type of cancer or subset of cancers, rather than being specific for a particular host cancer cell. It is therefore desirable to develop monoclonal antibodies which can be used in the diagnosis and treatment of human cancers.

2. Relevant Literature

Nowinski et al., *Science* (1980) 210:537–539 describe human monoclonal antibodies against Forssman antigen. Croce et al., *Nature* (1980) 288:488–489 describe human hybridomas secreting antibodies to measles virus. Olsson and Kaplan, *PNAS USA* (1980) 77:5429–5431 describe human-human hybridomas producing monoclonal antibodies of predefined antigenic specificity as well as the fusion partner employed for production of the antibodies. See also copending application Ser. No. 247,652, filed Mar. 26, 1981.

Schlom, *PNAS USA* (1980) 77:6841–6845 describes monoclonal antibodies for breast cancer and Sikora, *Brit. J. of Cancer* (1981) 43:696 describes separating in situ lymphocytes from a cancer providing antibodies specific for the cancer. In the Proceedings of the 15th Leukocyte Culture Conference, Parker and O'Brien, eds., Wiley Interscience, N.Y., Dec. 5–10, 1982, the subject hybridoma is described. This abstract is incorporated herein by reference.

SUMMARY OF THE INVENTION

Lymphocytes derived from a neoplastic human host are immortalized by fusion with human fusion partners to provide human x human hybridomas secreting monoclonal antibodies (MoAbs) specific for a cell surface antigen of a neoplastic cell. Particularly, monoclonal antibodies specific for antigens of solid tumor cells such as cervical cancer cells which are not found on normal cells of the same tissue type are provided for use in diagnostics and therapy.

DESCRIPTION OF SPECIFIC EMBODIMENTS

Human monoclonal antibodies (MoAbs) specific for antigens found on the surface of neoplastic cells from solid tumors are obtained from human x human fusions employing B lymphocytes, e.g., from lymph nodes draining a solid tumor. Particularly, lymph nodes are selected which appear to be active based on necrosis of tumor cells in the vicinity of the lymph node in an immunocompetent host.

The draining lymph node(s) may be isolated in conjunction with a variety of human tissue, e.g., cervix, mammary, colon, lungs, prostate, skin, etc.

The fusion partner may be any convenient immortalized human B-cell which does not secrete immunoglobulins or individual chains or fragments thereof, which can be selected against, as with HAT medium, and desirably which has a high fusion efficiency. Illustrative fusion partners are UC729-6, J-4 (SKO-007), and GM1500 6TG-A12.

The fusions may be performed as described in the literature employing PEG1500 as fusogen, plating the cells in HAT medium in a plurality of wells and then screening supernatants in the viable cell-containing wells for antibodies of interest. Wells positive for reactivity are then cloned by limiting dilution and expanded.

The hybridomas and monoclonal antibodies of this invention can find use in a variety of ways, particularly as sources of genetic material, as reagents, and as precursors to products which find use as reagents.

The subject hybridomas may be used as a source of genetic material. For example, the subject hybridomas may be fused with other fusion partners to provide novel hybridomas having the same secretory capabilities as the hybridomas providing the genetic material to provide antibodies having the same specificity. Such fusions may result in the production of antibodies having different heavy chains so as to provide the other classes or subclasses of antibodies, e.g., G. A, or M.

The monoclonal antibodies can be used in a variety of ways, both in vivo and in vitro diagnosis, as well as in therapy. For many applications, the antibodies will be labeled with a compound which imparts a desired property to the antibodies, such as providing a detectable signal, providing cytotoxicity, providing for localized electromagnetic radiation, or the like. Labels may include radionuclides, enzymes, fluorescers, toxins or the cytotoxic fragment of toxins, particles, metals, metalloids, etc. The antibodies may be incorporated in liposome membranes or modified with lipids, so as to be incorporated in such membranes. The antibodies by themselves or labeled, may be used in in vitro diagnosis for measuring the presence of antigens associated with a neoplasm such as cervical cancer, for in vivo diagnosis for introduction into a host, e.g., intravenously in a physiologically acceptable carrier, e.g., PBS, or may be introduced for therapeutic purposes in the same manner.

The antibodies by themselves or labeled, may also be used for treating a neoplasm in human host such as cervical carcinoma, prostate tumor, colon carcinoma, lung cancer, breast cancer or melanoma. The antibodies of this invention are easily soluble in physiological saline, and therefore can be injected intravenously or intramuscularly as a saline solution or a drip. Furthermore, the antibodies of the invention can be used in the form of an ointment or suppository.

The amount of antibody employed will vary depending upon the particular application. Introduction of antibodies for diagnostic and therapeutic purposes has been extensively described in literature.

The entire antibody need not be used, for many applications only a fragment having intact variable regions will suffice. For example, Fab fragments, F(ab')$_2$ fragments, or Fv fragments may suffice. Additionally, chimeric antibodies having the variable regions of the instant antibodies can be produced.

Exemplary of human-human hybridomas utilizing lymphocytes from draining lymph nodes are the novel hybridomas CLNH5, (on deposit with the A.T.C.C. with Accession No. HB 8206) and CLNH11, (on deposit with the A.T.C.C. with Accession No. HB 8307) hybridomas obtained from CLNH5 and 11, antibodies derived from such hybridomas, derivatives of such antibodies and the use of the antibodies and their derivatives for diagnosis and therapy. CLNH5 and 11 are obtained by fusion between the fusion partner UC729-6 with lymphocytes from lymph node cells of a patient having cervical cancer. UC729-6 is on deposit at the A.T.C.C. with Accession No. CRL 8061. UC729-6 was deposited for patent purposes in conjunction wish the filing of application Ser. No. 247,652.

The lymphocytes employed for that fusion were from a draining lymph node from a cervical carcinoma and peripheral blood lymphocytes from a patient having cervical carcinoma. The fusion was performed by combining the patient's lymphocytes from the lymph node with the fusion partner UC729-6 at a ratio of about 2:1 in a solution of about 35% polyethylene glycol in HEPES buffered RPMI 1640. The mixture of cells was then suspended in appropriate selective medium, particularly HAT medium containing about 10% fetal bovine serum, placed in wells at about $10^5$ cells per well and a sufficient time permitted for the cells to grow. The selective medium was replaced from time to time.

Wells from the above fusion provided clones specifically reactive with cell surface antigens of the cervical cancer cells of the host patient which were designated CLNH5 and 11. These wells provided human IgM and IgG monoclonal antibodies, respectively, which react with antigen found on a variety of cervical carcinomas and other tumor cell lines, e.g., small cell carcinoma of the lung, but not with normal tissues and normal cell lines, which were tested.

Additional fusions of lymphocytes from a lymph node draining a solid tumor were performed using lymph nodes from a patient with vulvar carcinoma and from a patient with a Wilm's tumor. In each fusion, a number of hybridomas secreting antibodies which reacted with cell surface antigens found on carcinoma cells and either not detectable on normal cells or found on normal cells in significantly reduced numbers were produced. Exemplary hybridomas are described in detail in the experimental section.

The fusion frequency for human lymphocytes from lymph nodes is higher than the fusion frequency using peripheral blood lymphocytes (1.9 in comparison to 0.51 hybrid+wells/ $10^6$ lymphycytes mean fusion rate; See Glassy et al., p. 211–225 in *Human Hybridomas and Monoclonal Antibodies*, Plenum Publishing Corp. 1985, Engleman et al., eds.). In addition to the enhanced fusion frequency, it has been found that hybridomas can be selected from fusions of lymphocytes from draining lymph nodes which secrete antibodies that bind to antigens which are found on tumor cells, but not to normal cells of the same tissue type. Usually the antibodies bind to antigens found on a number of tumor cells of different tissue types and do not exhibit any substantial binding to a wide variety of normal cells. The hybridomas are stable, retaining parental DNA and maintaining an Ig secretion rate for over a year in culture.

The following examples are offered by way of illustration and not by way of limitation.

EXPERIMENTAL

EXAMPLE 1

MATERIALS AND METHODS

Fusion and Selection of Hybridomas

Lymph nodes were teased with nugent forceps in RPMI 1640 media and isolated lymphocytes were cultured overnight at 37° C. and 5% $CO_2$ in RPMI 1640 with 10% fetal calf serum (FCS) and 2mM L-glutamine. Lymphocytes were counted and mixed at a ratio of 2:1 with the human lymphoblastoid B cell line UC729-6 (Handley and Royston, 1982, in Hybridomas in Cancer Diagnosis and Treatment, eds. Mitchel and Oettgen, pp. 125–132, Raven Press, N.Y.), then fused with polyethylene glycol 1500 by a modification of the technique by Gefter et al., *Somatic Cell Genetics* (1977) 3:321–336. Fused cells were plated at $10^5$ cells/well in a Costar 96 well microtiter plate with Hypoxanthine-Amethopterin-Thymidine (HAT, Littlefield, *Science* (1964) 145:709–710) supplemented RPMI 1640 with 10% FCS and L-glutamine. Within 10–20 days, wells positive for hybridoma growth were assayed for human antibody production and their reactivity to a limited human cell panel by an enzyme immunoassay (EIA). Wells positive for reactivity were cloned by limiting dilution without the use of feeder layers and expanded for further study.

Enzyme Immunoassay

Human MoAbs and their reactivity to cells were detected by a modification by an EIA previously described (Handley et al., *J. of Immunologic Methods* (1982) 54:291–296, as modified by Glassy et al., *J. Immunologic Methods* (1983) 58:119–126). Briefly, 50 μl of either an affinity purified goat anti-human Ig or a $4 \times 10^6$ target cell/ml suspension was immobilized in triplicate wells of an immunofiltration manifold. (The specially designed microtiter plate which serves as both an incubation chamber and filtration manifold (VP no. 107) is available commercially from V and P Scientific, San Diego, Calif.). The bottom of each well contains a 0.6 mm hole over which is placed a 6 nm diameter glass fiber filter. Surface tension prevents fluid volumes less than 100 µl from draining through the hole until a vacuum is applied. When vacuum is applied, fluid is drawn through the filter and out the drain hole leaving particulate matter trapped on the filter. After washing 3x with 0.3% gelatin in phosphate buffered saline, 50 µl of hybridoma supernatant were incubated 30 min. at room temperature. Filters were then washed and incubated with 50 µl of a horseradish peroxidase-conjugated goat anti-human Ig for an additional 30 min. Filters were washed again and incubated with 150 µl of a 400 µg/ml solution of orthophenylene diamine in citrate buffer. 100 µl of each well were then transferred to a new plate containing 50 µl of 2.5 M $H_2SO_4$ and read on a Dynatek (Alexandria, Va.) MR 580 micro-ELISA reader at 492 nm.

Hybridoma culture fluids were precipitated with 50% ammonium sulfate and crude Ig fractions collected. The precipitates were dissolved in physiological saline and purified by affinity chromatography using *S-aureus* Protein A-bound Sepharose with IgG and Sepharose-(sheep anti (humanIgM) antibody) with IgM. From 1L of the culture fluid of CLNH5, 2.2 mg IgM was obtained, while from 1L of the culture fluid of CLNH11, 3.0 mg IgG was obtained.

RESULTS

Table 1 outlines the results of the fusion attempting to produce anti-SCCC (squamous cell carcinoma of cervix) human MoAbs. The fusion producing CLNH5 and CLNH11, human-human hybridomas secreting a MoIgMk and a MoIgG reactive with SCCC cell lines, generated 6 growth positive wells of 80 wells plated. Hybridomas CLNH5 and CLNH11 were cloned and expanded when found to react with the cervical carcinoma cell lines, CaSki and Hela.

TABLE 1

GENERATION AND IDENTIFICATION OF HUMAN MoAbs

| Lymph Node draining | #Lymphocytes fused | #Hybridomas generated | #Secreting M G A | #Human reactive |
|---|---|---|---|---|
| Cervical Carcinoma (SCCC) | 7.0 × 10⁶ | 6 | 2 1 0 | 2 (CLNH5 and 11) |

The relative amounts of human MoAb bound to each of the cell lines listed was measured by EIA.

Antibody (IgM) secreted by CLNH5 shows positive reactivity with carcinomas of the cervix (CaSki, Hela), lung (T293, Calu-1, and Sk-MES-1), melanoma (SK-MEL-28), and prostate (LnCap) and was negative for normal fibroblasts, T lymphocytes and peripheral blood lymphocytes. Antibody (IgG) secreted by CLNH11 shows positive reactivity with carcinomas of the cervix (CaSki, Hela), prostate (PC-3), breast (ZR-76-1), colon (COLO-205) and melanoma (G-361) and was negative for normal fibroblasts (WI-38 and MRC-9), T. lymphocytes and peripheral blood lymphocytes.

The cytobiochemical properties of the hybridomas of the present invention are shown below.

Hybridoma CLNH5:

Hybridomas CLNH5 was deposited at the American Type Culture Collection (ATCC), 10801 University Boulevard, Manassas, Va. 20110-2209 on Jan. 28, 1983 and received ATCC Accession No. HB 8206. Hybridoma CLNH11 was deposited at the ATCC on May 20, 1983 and received ATCC Accession No. HB 8307.

(1) Number of chromosomes: 60 to 90 (maximum frequency 80).

(2) It secretes human immunoglobulin M (IgM).

(3) Doubling time: 30–40 hours.

(4) Lymphocytic single cell.

(5) Its DNA content is at least two times, for example, 2 to 2.5 times, that of normal human lymphocytes.

(6) IgM binds to human cervical carcinoma cells and the other carcinomas mentioned above.

In addition, the above hybridoma CLNH5 can be proliferated in HAT medium (medium containing hypoxanthine, amethopterin and thymidine).

Hybridoma CLNH11:

(1) Number of chromosomes: 60 to 90 (maximum frequency 80).

(2) It secretes human immunoglobulins G (IgG).

(3) Doubling time: 30–40 hours.

(4) Lymphocytic single cell.

(5) Its DNA content is at least two times, for example 2 to 2.5 times, that of normal human lymphocytes.

(6) IgG binds to human cervical carcinoma cells, and the other carcinomas mentioned above.

In addition, the above hybridoma CLNH11 can be proliferated in HAT medium.

The relative DNA content (the ratio to the DNA content of normal human lymphocytes) was determined by a method which comprises dyeing the hybridoma and then analyzing it by a cytofluorometer.

The properties of the monoclonal human immunoglobulins in accordance with this invention are shown below.

Monoclonal Human Immunoglobulin Produced by the Hybridoma CLNH5

(a) It is human immunoglobulin M (IgM).

(b) It has a stronger binding affinity to cell lines, Hela and CaSki, than to normal fibroblasts (WI-38).

(c) It does not react with human red blood cells, nor shows an agglutination reaction on human red blood cells.

(d) It is composed of heavy chains (H chains) and light chains (L chains), has a molecular weight of about 180,000 (monomer), and exists as a pentamer in the culture fluid.

Monoclonal Human Immunoglobulin Produced by the Hybridoma CLNH11

(a) It is human immunoglobulin G (IgG).

(b) It has a stronger affinity to cell lines, Hela and CaSki, than to normal fibroblasts (WI-38).

(c) It does not react with human red blood cells, nor shows an agglutination reaction on human red blood cells.

(d) It is composed of H chains and L chains and has a molecular weight of about 150,000.

The binding activity of human monoclonal antibodies distinguishing neoplastic cells from normal cells was measured as follows:

An original human tissue section including carcinoma cells and normal cells was fixed on a glass plate by glutaraldehyde, and then stained by enzyme immunoassay according to the method of Sternberger el al., *J. Hist. Cyto.* (1970) 18:315.

EXAMPLE 2

The fusion and cloning procedure described in Example 1 were used in preparing the hybridoma described in Example 2. An involved lymph node from a patient who had invasive squamous cell carcinoma of the vulva was received within three hours of surgery. The nodal segments were immersed in serum-free RPMI-1640, trimmed free of extraneous tissue and capsular components, and teased with nugent forceps to make a single cell suspension. After large tissue aggregates settled, the cells in suspension were removed and washed twice, pelleting the cells at 500 x g for 5 min/wash. All dissections and cell preparations were performed at room temperature. The isolated lymphocytes were resuspended at $5 \times 10^6$/ml in RPMI-1640 media supplemented with 10% fetal calf serum (FCS) and incubated overnight at 37° C. in 5% $CO_2$ prior to fusion.

Using 35% polyethylene glycol 1500, $3.33 \times 10^7$ of the patient's lymphocytes were fused with $1.66 \times 10^7$ UC 729-6 cells according to the procedure described above. After the fusion, the cells were added to 96-well plates at $1.0 \times 10^5$ cells per well. The day after the fusion, the growth media was replaced by RPMI-1640 media supplemented with 10% FCS and glutamine, including hypoxanthine ($1 \times 10^{-4}$ M), amethopterin ($2 \times 10^{-7}$ M, and thymidine ($1.6 \times 10^{-5}$ M) (HAT media)(13). After 2–4 weeks in culture, hybrids visible to the eye were analyzed for human Ig secretion. Eighty hybrids resulted from 480 wells plated, 14 of which secreted IgG and four of which secreted IgM.

The hybridoma supernatants were screened as in Example 1. Those which secreted Ig were expanded and cloned by limiting dilution without any feeder layer cells in RPMI media.

Cryopreservation and thawing of these hybridomas did not result in any detectable adversity in stability and secretion. The hybrids generated were tetraploid as judged by karyotypic and cytofluorographic analysis of their DNA content (Table 2).

TABLE 2

CYTOFLUOROGRAPHIC ANALYSIS OF HUMAN HYBRIDOMA DNA

| | Relative DNA Content[a] | | | | |
|---|---|---|---|---|---|
| Cell Type | 2 months | 4 months | 8 months | 12 months | 24 months |
| UC 729-6 | 45 ± 2 | 44 ± 2 | 45 ± 4 | 45 ± 2 | 45 ± 2 |
| VLN3G2 | 80 ± 2 | 81 ± 3 | 80 ± 4 | 80 ± 3 | N.D. |
| VLN1H12 | 82 ± 3 | 81 ± 3 | 81 ± 3 | 80 ± 3 | N.D. |
| CLNH5[b] | 83 ± 3 | 82 ± 2 | 83 ± 3 | 83 ± 3 | 82 ± 3 |
| MHG7[c] | 74 ± 2 | 68 ± 3 | 55 ± 3 | 54 ± 3 | 51 ± 2 |

[a]Relative DNA content of UC 729-6 and the hybridomas was obtained by the propidium iodine method (Glassy et al., Proc.Natl.Acad.Sci.USA (1983) 80:6327). At the indicated times after fusions, the DNA content of the cells was determined.
[b]CLNH5 is described in Example 1.
[c]MHG7 is a mouse-human hybridoma described in Lowe et al., J.Urol. (1984) 132:780.

HLA phenotyping has also shown that these human hybridomas express antigens of both parental UC 729-6 and the patient's lymph node lymphocytes (Table 3).

TABLE 3

HLA PHENOTYPE OF UC 729-6 AND VLN HYBRIDS

| Cell Line | HLA-A | HLA-B | HLA-DR |
|---|---|---|---|
| UC 729-6 | A1, A2 | B5, B17 | DR4, DR7 |
| VLN3G2 | A1, A2 | B5, B17 B27, BW44 | DR4, DR7 |

TABLE 3-continued

HLA PHENOTYPE OF UC 729-6 AND VLN HYBRIDS

| Cell Line | HLA-A | HLA-B | HLA-DR |
|---|---|---|---|
| VLN1H12 | A1, A5 | B5, B17 B27 | DR4, DR7 |

Because large amounts of antibody would be required in a clinical setting, the long-term stability of human Ig-secreting hybridomas was studied. The issue of long-term stability of these VLN hybrids was assessed over a 12-month period, during which both DNA content (Table 2) and Ig secretion rate (Table 4) were examined. The generated data indicated that UC 729-6 is a genetically stable vector for the capture and immortalization of human B lymphocytes.

TABLE 4

IgM SECRETION ($\mu$g IgM/$10^6$ cells/ml/day) BY HUMAN HYBRIDOMAS OVER TIME

| Time (Months) | VLN1H12 | CLNH5 | MHG7 |
|---|---|---|---|
| 1 | 1.58 | 2.36 | 2.84 |
| 2 | ND | 2.48 | 2.60 |
| 3 | 1.37 | ND | 1.92 |
| 4 | ND | 2.28 | 1.45[a] |
| 5 | ND | ND | 2.11 |
| 6 | 1.25 | 2.43 | 1.87 |
| 7 | ND | ND | 1.49 |
| 8 | 1.29 | 2.36 | ND |
| 9 | ND | ND | 1.16[a] |
| 10 | 1.31 | 2.43 | 2.48 |
| 11 | ND | ND | 2.27 |
| 12 | 1.28 | 2.24 | 2.06 |

At the indicated yime points after the fusion, the amount of human IgM in the culture supernatant was determined by EIA. ND = not determined.
[a]MHG7, a mouse-human hybridoma described in Table 2, was subcloned by limiting dilution (1 cell/3 wells) at 4 and 9 months post-fusion to sleect for a hugher secreting subclone.

Immunoreactivity

Of the 14 IgG-secreting hybrids, six passed initial reactivity screens against target cell bound antigens, whereas one of the four IgM-secreting hybrids passed. These seven hybridomas were cloned by limiting dilution (1 cell/3 wells) and expanded for further analysis. The reactivity index (R1) of the six IgG human MoAbs against a panel of normal and malignant cells was calculated from the following formula:

$$RI = \frac{O.D._{490} \text{ test } MoAb - O.D._{490} \text{ background}}{O.D._{490} \text{ control } MoAb - O.D._{490} \text{ background}}.$$

The control consisted of an irrelevant human IgG used at the same concentration as the test human MoAb.

These six IgG MoAbs have broad reactivity pro-files with human carcinoma cells, but do not react with hematopoietic or fibroblast cell lines and normal peripheral blood leukocytes. Of particular note, all six of the IgGs were very reactive with the A431 cell line, a carcinoma of the vulva, similar to the primary cancer of the patient used in these studies.

A titration of the VLN3G2 and VLN5C7 IgG MoAbs against target cell-bound antigens was determined. Starting from an initial concentration of 450 ng/ml of VLN3G2 appreciable reactivity was obtained even at 450 pg/ml. There did not appear to be any major quantitative differences in the antigen expression by either the vulva, lung, or stomach cell lines since the reactivity of the MoAbs was similar in each case.

Target A431 cells were analyzed by indirect immunofluorescence with VLN3G2. Cell surface and cytoplasmic staining patterns were evident.

EXAMPLE 3

The hybridomas described in Example 3 were prepared in the same manner as the hybridomas of Example 1. The hybridoma designated WLNA6 was prepared from lymphocytes isolated from a lymph node draining a Wilm's tumor. A Wilm's tumor is a malignant renal tumor which has frequently metastasized to the lungs or elsewhere when a renal mass is located.

CLNH5 and WLNA6 were studied because the supernatants reacted with a number of cell lines (Table 5).

carcinoma cell lines, HT-29, T-84; kidney cell line, Caki-2; carcinomas of the bladder, T-24, Scaber; stomach carcinoma cell lines, AGS-10, AGS, Kato-III, MKN-74, MKN-28; vulva carcinoma cell line, A431; ovarian carcinoma cell line, SK-OV-3; prostatic carcinoma cell lines, DU 145, PC-3, Ln-Cap; cervical carcinoma cell lines, Hela and Caski; murine myeloma P3-NS-1-Ag4-1; and murine IT22 fibroblasts.

Cell Surface Phenotyping

Cell surface phenotypes of UC 792-6, MHG7, CLNH5, and VLN1H12 were analyzed by indirect immunofluorescence using procedures and reagents previously described in Royston et al., *J. Immunol.* (1980) 125:715.

Cytofluorographic Analysis of DNA Content

Cells and hybridomas were stained by the propidium iodide method for the determination of relative cell DNA

TABLE 5

REACTIVITY OF HUMAN MoAbS WITH HUMAN CELL LINES

| | | $OD_{490}$ | | |
|---|---|---|---|---|
| Cell Line | Type | 8A1 | CLNH5 | WLNA6 |
| Calu-1 | Lung carcinoma | 0.031 ± 0.008 | 0.342 ± 0.061 | 0.029 ± 0.009 |
| Sk-MES-1 | Lung carcinoma | 0.025 ± 0.007 | 0.395 ± 0.054 | ND |
| T293H | Lung carcinana | 0.011 ± 0.005 | 0.498 ± 0.081 | 0.753 ± 0.225 |
| HeLa | Cervical carcinoma | 0.029 ± 0.010 | 0.443 ± 0.075 | 0.140 ± 0.041 |
| CaSki | Cervical carcinoma | 0.021 ± 0.009 | 0.429 ± 0.084 | 0.145 ± 0.073 |
| Ln-Cap | Prostate carcinoma | 0.033 ± 0.007 | 0.386 ± 0.041 | 0.005 ± 0.003 |
| 350Q | Normal fibroblast | 0.040 ± 0.011 | 0.026 ± 0.008 | 0.041 ± 0.014 |
| WI-38 | Normal fibroblast | 0.034 ± 0.088 | 0.038 ± 0.009 | 0.033 ± 0.015 |

$OD_{490}$ values were read on a Dynatech micro-ELISA reader (model MR 580) in a quantitative immunofiltration assay (23). Values represent mean ± SD of triplicate determinations. ND, not determined.

The CLNH5 IgM MoAb reacted with several human malignant cell lines of cervical, lung, and prostate origin but not with normal human fibroblasts. The WLNA6 IgM MoAb reacted strongly with T293, an oat cell carcinoma of the lung, had weak reactivity with the HeLa and CaSki cervical carcinoma cell lines, and had no reactivity with lung carcinoma Calu-1, prostate carcinoma Ln-Cap, or WI-38 and 350Q normal fibroblasts.

The 8A1 IgM MoAb failed to react with any of the tested cell lines and served as a negative control. 8A1 is a hybridoma produced from the fusion UC 729-6 and the peripheral blood lymphocytes of a patient with chronic lymphocytic leukemia.

EXAMPLE 4

As described previously, human lymphocytes obtained from regional draining lymph nodes of patients with cancers of the cervix, kidney and vulva were fused with a human fusion partner, UC729-6, to produce hybridomas designated CLNH5, WLNA67 and VLN1H:12, respectively. Human lymphocytes from a regional hymph node of a patient with prostate cancer was fused to a mouse fusion partner, P3-NS-1-Ag4-1, using the same fusion protocol.

The hybridomas and their secreted antibodies were-analyzed to determine the genetic stability of the hybridomas. The following materials and methods, in addition to those previously described, were used.

Cell Lines

The following human cell lines were used in Example 4. Leukemia cell lines, Molt-4, CEM, HPB-A11, K562, ML-3, KG-1, and 8402; melanoma cell lines, M21, MEWO, SK-MEL-28; macrophage cell line U937 (kindly provided by Dr. K. Nilsson); normal fibroblasts, 350Q, WI-38; colon content and analyzed by cytofluorometry, as described in Taylor, *J. Histochem. Cytochem.* (1980) 28:1021. Briefly, $1.0 \times 10^6$ cells were fixed in 70% ethanol for 2 hours, washed (500 x g for 10 minutes), and suspended in 100 $\mu$l PBS. One milliliter of propidium iodide (0.05 mg/ml) (Sigma) was added to the cell suspension, incubated for 15 minutes at 4° C., and filtered through a 50 $\mu$m pore nylon mesh. Samples were analyzed on an Ortho Cytofluorograf 50H with computer 2150 equipped with a 488 mm argon laser at 400 mW. All data were generated by the computer.

Isozyme and Karyotype Analysis

The presence of unique isozyme patterns from human chromosomes were determined by established procedures (Glassy et al., *Cancer Res.* (1982) 42:3971; Kamarck et al., *Exp. Cell Res.* (1984) 152:1). Human chromosome 2 was identified by malate dehydrogenase (E. C. 1.1.1.37) and human chromosome 14 was identified by nucleoside phosphorylase (E. C. 2.4.2.1).

The antibody secretion rates of the human-human hybridomas was compared to that of the mouse-human hybridoma over a 12-month period. IgM secretion of CLNH5 and VLN1H12 was relatively stable at 2.5 $\mu$g/ml and 1.5 $\mu$g/ml, respectively, over the time period indicated. MHG7, the mouse human hybrid, however, required subcloning at three and eight months in culture to retain antibody secretion. Cultures of MHG7 not subcloned routinely lost antibody production entirely. Subcloning of MHG7 generated clones of greater antibody production capability and clones entirely lacking antibody production. Isoenzyme analysis of some subclones of MHG7 (Table 6) revealed the presence of both human chromosomes 2 and 14 in those producing human IgM whereas those clones lacking either chromosome 14 or 2 and 14 produced no detectable IgM. Human chromosomes 2 and 14 are known to contain the loci for kappa light chain (McBride et al., *J. Exp. Med.* (1982) 155:1480) and Ig heavy chain (Croce et al., *Acad. Sci (USA)* (1979) 76:3416), respectively.

TABLE 6

Isoenzyme Analysis of MHG7

| Human Chromosome | | MHG7 Subclone | Amount Human IgM Secreted (ng/ml) |
|---|---|---|---|
| 2 | 14 | | |
| − | − | MHG7M.1.1 | <32[a] |
| + | − | MHG7M.1.2 | <32 |
| + | + | MHG7M.1.3 | 1850 |
| + | + | MHG7M.1.4 | 1100 |
| − | + | MHG7M.1.5 | >32 |

[a]The lower limit of the EIA used was 32 ng/ml. Mid-log phase cells were harvested from culture and somatic cell hybrid isoenzymes were characterized electrophoretically on cellulose acetate gels according to standard procedures (Glassy et al., CancerRes. (1982) 42:3971; Kamarck et al., Exp.Cell.Res. (1984) 152:1) and analyzed by EIA for the amount of human IgM secreted (see Materials and Methods).

Relative DNA contents of the human Ig secreting hybridomas are shown in Table 7.

TABLE 7

Cytofluorographic Analysis of Human Hybridoma DNA

| | Relative DNA Content[3] | | | | |
|---|---|---|---|---|---|
| Cell Type | 2 mo | 4 mo | 8 mo | 12 mo | 24 mo |
| UC 729-6 | 45 ± 2 | 44 ± 2 | 45 ± 2 | 45 ± 2 | 45 ± 2 |
| CLNH5 | 83 ± 3 | 82 ± 2 | 83 ± 3 | 83 ± 3 | 83 ± 3 |
| VLN3G2 | 80 ± 3 | 81 ± 3 | 80 ± 4 | ND | ND |
| MHG7 | 74 ± 2 | 68 ± 3 | 55 ± 3 | 54 ± 3 | 51 ± 2 |
| VLN1H12 | 82 ± 3 | 81 ± 3 | 81 ± 3 | ND | ND |

[a]Relative DNA contents of UC 729-6, human-human hybrid MHG7 were obtained by the propidium iodide method (Taylor. J.HistochemCytochem. (1980) 28:1021). At the indicated times after fusions, the DNA contents of the cells were recorded. NH = not determined.

Over a two-year period, the tetraploid hybridoma CLNH5 and the heteroploid mouse-human hybrid MHG7 were compared with the diploid UC 729-6. The DNA contents of CLNH5 and UC 729-6 have been relatively stable over 24 months in culture while MHG7 had lost a significant number of chromosomes over the same period of time.

The surface marker phenotype of UC 729-6 and hybrids are shown in Table 8.

TABLE 8

Cell Surface Phenotypes[a]

| Phenotypic Marker | Function | % Positive Cells | | | |
|---|---|---|---|---|---|
| | | UC 729-6 | MHG7 | CLNH5 | VLN1H12 |
| Control | — | 3 | 12 | 2 | 2 |
| T101 | pan T-cell | 2 | 11 | 2 | 2 |
| Leu4 | pan T-cell | 4 | 13 | 2 | 3 |
| Leu3 | helper T-cell | 4 | 11 | 2 | 3 |
| Leu2 | suppressor T-cell | 4 | 15 | 3 | 5 |
| I$_2$ | HLA-DR | 97 | 12 | 98 | 100 |
| BA1 | pan B-cell | 7 | 11 | 3 | 4 |
| BA2 | hematopoietic precursor | 4 | 10 | 62 | 67 |
| BA3 | common ALL | 4 | 11 | 1 | 3 |

TABLE 8-continued

Cell Surface Phenotypes[a]

| Phenotypic Marker | Function | % Positive Cells | | | |
|---|---|---|---|---|---|
| | | UC 729-6 | MHG7 | CLNH5 | VLN1H12 |
| sIg | immunoglobulin | + | + | + | + |

[a]Mid log-phase cells were harvested from culture and analyzed on an Ortho Cytofluorograf 50H and computer system 2150 using reagents and procedures previously described in Royston et al., J.Immunol. (1980) 125:715. sIg was assessed using indirect immunofluorescence under a fluorescence microscope (Royston et al., supra).

The most significant finding was the expression on the human hybrids of the BA2 antigen associated with precursor hematopoietic cells. This antigen was not expressed on UC 729-6.

Reactivity of Human Monoclonal IgM

The reactivity of WLNA6 with a panel of human cell lines was determined. Five other human IgM monoclonals generated in the same fusion as WLNA6, and deemed of interest in an initial screen, failed an expanded screen. WLNA6 was reactive with 3 of 15 cell lines tested, the highest activity being T293H, a squamous cell carcinoma of the lung.

The reactivity of the monoclonal IgM antibodies from CLNH5, VLN1H12, and MHG7 with a larger panel of cell lines was determined. The reactivity index was calculated as follows:

$$RI = \frac{O.D.490 \text{ test } MoAb - O.D.490 \text{ background}}{O.D.490 \text{ irrelevant } MoIg - O.D.490 \text{ background}}$$

By these criteria, CLNH5 was reactive with 8 of 31 cells tested; these being carcinomas of the cervix (CaSki, Hela), lung T293H, Calu-1, and SK-MES-1), melanoma (SK-MEL-28), prostate (LnCap), and vulva (A431), VLN1H12 was reactive with 15 of 27 cell lines tested; carcinomas of the cervix (CaSki, Hela), kidney (Caki-2), lung (NCI-69, T293H), melanoma (SK-MEL-28), pancreas (Capan-1). prostate (LnCap, PC-3, DU-45), stomach (MNK-28, KATO-III, AGS-10, AGS), and vulva (A431) were all reactive. MHG7 was reactive with 8 of 37 cell lines tested; carcinomas of the colon (T-84), lung (T293H, T222, T291), prostate (LnCap, PC-3), stomach (Kato-III), and vulva (A431) were positive.

Titrations of MHG7, CLNH5, and VLN1H12 against cell-bound target antigens are shown in Table 9. With as few as $2 \times 10^3$ target cells/well, the EIA detected as little as 20 ng of cell-bound human IgM MoAb.

TABLE 9

Titration of Human Monoclonal Antibodies Against Cell-Bound Target Antigens[a]

| MoAb | Cell Line[b] | | | | |
|---|---|---|---|---|---|
| MHG7 | Ln-Cap | CLNH5 | CaSki | VLN1H12 | A431 |
| 3100[c] | 0.465 | 2000 | 0.441 | 1450 | 0.325 |
| 620 | 0.396 | 400 | 0.373 | 290 | 0.174 |
| 124 | 0.271 | 80 | 0.229 | 58 | 0.171 |
| 25 | 0.121 | 16 | 0.229 | 12 | 0.146 |
| 5 | 0.095 | 3.2 | 0.084 | 3 | 0.144 |

TABLE 9-continued

Titration of Human Monoclonal Antibodies
Against Cell-Bound Target Antigens[a]

| | MoAb Cell Line[b] | | | | |
|---|---|---|---|---|---|
| MHG7 | Ln-Cap | CLNH5 | CaSki | VLN1H12 | A431 |
| 1 | 0.102 | 0.64 | 0.084 | 1.5 | 0.149 |
| | Background: 0090 | | Background: 0.085 | | Background: 0.145 |

[a]Cells were used in the EIA at $2.0 \times 10^3$ cells/well. (See Materials and Methods).
[b]The cell line used with each MoAb is allogeneic with the patient's cancer from which the lymph nodes were obtained. MHG7 was derived from prostate cancer and Ln-Cap is a prostate carcinoma cell line. CLNH5 from cervical cancer and CaSki is a carcinoma of the cervix; VLN1H12 from vulva cancer and A431 is a carcinoma of the vulva.
[c]Concentration of human IgM is expressed in ng/ml.

The subject monoclonal antibodies are useful for diagnosing, imaging and potentially for treating cervical carcinoma as well as other reactive tumors. Because of the specificity of the monoclonal antibodies over a range of cervical carcinomas from different hosts, the subject antibodies can be used in different hosts, rather than solely with the host source of the antigen. Similarly, the monoclonal antibodies frequently are useful to identify carcinomas of a number of tissue types in addition to the type of tumor of the host source of the lymphocytes. Because the subject antibodies are human, they are less likely to produce a significant immune response when employed in in vivo diagnosis or therapy.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of a neoplasm, the method comprising:

contacting a sample suspected of containing a neoplasm with a monoclonal antibody, or a fragment thereof, having the same binding specificity as that of the monoclonal antibody expressed by cell line selected from group consisting of CLNH 11 (ATCC Accession No: HB8307), and CLNH5 (ATCC Accession No: HB8206); and detecting the presence of binding of the monoclonal antibody to the sample.

2. The method of claim 1, wherein the binding is detected by detecting a signal from a detectable label on said monoclonal antibody or fragment thereof.

3. The method of claim 2, wherein said label is selected from the group consisting of an enzyme, a radionuclide, and a fluorochrome.

4. The method of claim 1, wherein said neoplasm is selected from the group consisting of a cervical carcinoma, prostate carcinoma, lung cancer, breast cancer, kidney cancer, stomach cancer, vulva cancer, or melanoma.

5. The method of claim 1, wherein the monoclonal antibody, or fragment thereof, has the same binding specificity as that of the monoclonal antibody expressed by CLNH11 (ATCC Accession No: HB8307).

6. The method of claim 1, wherein the monoclonal antibody, or fragment thereof, has the same binding specificity as that of the monoclonal antibody expressed by CLNH5 (ATCC Accession No: HB82306).

* * * * *